United States Patent [19]

McArthur

[11] 4,024,171

[45] May 17, 1977

[54] ALUMINUM BORATE CATALYST COMPOSITIONS AND USE THEREOF IN CHEMICAL CONVERSIONS

[75] Inventor: Dennis P. McArthur, Yorba Linda, Calif.

[73] Assignee: Union Oil Company of California, Los Angeles, Calif.

[22] Filed: Jan. 19, 1976

[21] Appl. No.: 650,513

Related U.S. Application Data

[60] Division of Ser. No. 591,352, June 30, 1975, which is a continuation of Ser. No. 307,031, Nov. 16, 1972, abandoned.

[52] U.S. Cl. .................. 260/449.6 M; 252/432; 252/373; 423/213.2; 423/213.5; 260/666 A; 260/668 D; 260/673; 260/676 R; 260/677 H; 208/16; 208/133; 208/209; 208/254 R
[51] Int. Cl.² ........................................ C07C 1/04
[58] Field of Search ............... 260/449 M, 449.6 M

[56] References Cited

UNITED STATES PATENTS

| | | | |
|---|---|---|---|
| 2,118,143 | 5/1938 | Benner et al. | 423/279 |
| 3,156,657 | 11/1964 | Pinder | 252/466 J |
| 3,172,866 | 3/1965 | Belon | 252/463 |
| 3,331,787 | 7/1967 | Keith et al. | 252/439 |
| 3,361,535 | 1/1968 | Pollitzer et al. | 260/449 M X |
| 3,379,505 | 4/1968 | Holmes et al. | 260/449 M X |
| 3,450,514 | 6/1969 | Sinfelt et al. | 260/449 M |
| 3,549,556 | 12/1970 | Dienes | 260/449 M X |
| 3,890,113 | 6/1975 | Child | 260/449 M X |

*Primary Examiner*—Howard T. Mars
*Attorney, Agent, or Firm*—Lannas S. Henderson; Richard C. Hartman; Dean Sandford

[57] ABSTRACT

Certain crystalline aluminum borate catalyst supports containing about 8–25 weight-percent of $B_2O_3$ are found to provide unusually stable and active catalysts for high-temperature chemical conversions, particularly exhaust gas conversion, when prepared by precalcining shaped composites of alumina and boria at temperatures between about 1250° and 2600°F, prior to the addition thereto of active metal or metals. Calcination at below 1250° F is found to yield amorphous catalysts of inferior activity, while at temperatures above 2600° F drastic reductions in surface area may occur.

9 Claims, No Drawings under the type of active metals present. They are also highly resistant to shrinkage at temperatures up to at least about 2500° F.

ALUMINUM BORATE CATALYST COMPOSITIONS AND USE THEREOF IN CHEMICAL CONVERSIONS

RELATED APPLICATIONS

This application is division of Ser. No. 591,352, filed June 30, 1975, which in turn is a continuation of application Ser. No. 307,031, filed Nov. 16, 1972, now abandoned.

BACKGROUND AND SUMMARY OF INVENTION

It has long been the practice in the art to impregnate or otherwise distribute active catalytic metals upon support materials having desired properties of porosity, surface area, thermal and mechanical stability, and suitably inert chemical properties. All of these characteristics of the support are interrelated and contribute in an open unpredictable manner to the ultimate activity of the final catalyst in its intended use. Much effort has been devoted in recent years to the finding of a support material which will withstand the severe mechanical and thermal stresses encountered in catalytic converts for the conversion of nitrogen oxides, carbon monoxide, and unburned hydrocarbons in automobile exhaust gases. Some materials, e.g., alpha alumina, are suitably inert and stable, but in general do not give a final catalyst having the volumetric activity that can be obtained from the same quantity of active metal or metals supported on other less stable supports such as gamma alumina. An optimum combination of activity and stability has been difficult to achieve.

Alumina-boria catalyst composites are known in the art, and in particular were extensively investigated at one time in the catalytic cracking art. However it was in general considered desirable to retain a substantial surface area, above about 150 m²/g in the final catalyst composite, and for this reason it was the practice to calcine such catalysts at relatively low temperatures, below about 1200° F, which are below the temperature required for the formation of crystalline aluminum borates. At the other extreme, U.S. Pat. No. 3,172,866 discloses catalyst supports prepared by calcining alumina-boria mixtures containing less than 5 weight-percent boria at temperatures of 1600°–1800° C (2912°–2372° F), under which conditions the boria is apparently sublimed out of the composite, and a final alpha alumina support having a surface area below 0.5 m²/g is produced.

It has now been found that for purposes of producing a catalyst of maximum activity and stability for high temperature, vapor phase conversions such as exhaust gas conversions, a much superior support is produced by calcining certain alumina-boria composities within the temperature range of about 1250°–2600° F. Calcination within the range appears to produce a definite crystalline phase of $9Al_2O_3 \cdot 2B_2O_3$ and also in most cases a crystalline phase of $2Al_2O_3 \cdot B_2O_3$. Although calcining such composites at temperatures below or above the specified range can produce supports of adequate stability for some purposes, it appears that within the range of about 1250°–26000° F, an optimum combination of crystallinity, porosity, surface area, and/or chemical properties is produced, such that a distinct maximum activity is achieved from active metals supported on such supports. Also, such catalysts exhibit excellent thermal and mechanical stability up to temperatures of about 2500°–3000° F, depending mainly upon the type of active metals present. They are also highly resistant to shrinkage at temperatures up to at least about 2500° F.

DETAILED DESCRIPTION

Suitable alumina starting materials for the supports of this invention may comprise any one or more of the so-called "transition" aluminas, including species now commonly identified as chi, delta, eta, gamma, kappa, and theta aluminas. The various hydrated aluminas such as boehimite, gibbsite and bayerite may also be utilized. Alpha alumina may also be utilized in applications not requiring a high surface area. The preferred aluminas are the hydrated and/or transition forms having a specific surface area in the range of about 150–500 m²/g.

The boria component of the support may be added as powdered $B_2O_3$, or as a thermally decomposable precursor thereof such as orthoboric acid, tetraboric acid, metaboric acid, ammonium pentaborate, ammonium tetraborate, various organic compounds of boron such as the boric acid esters, alkyl boranes and the like. The preferred $B_2O_3$ source is ordinary orthoboric acid, $H_3BO_3$. The proportion of boron compound employed should be adjusted to provide a finished catalyst support wherein the weight ratio of $B_2O_3/Al_2O_3$ is between about 8/92 and 25/72, preferably between about 10/90 and 20/80. If the final composition contains more than 25 weight-percent $B_2O_3$, a liquid phase will be formed at calcination or conversion temperatures above 470° C (878° F), with resultant fluxing and loss of surface area and porosity (*Nature*, vol. 195, July 7, 1962, pages 69–70). A liquid phase is also formed at temperatures above 1035° C (1895° F) is more than 14 weight-percent of $B_2O_3$ is present, but in the $B_2O_3$ concentration range of 14–25 percent, this liquid phase is not necessarily detrimental. A minimum of about 8 weight-percent $B_2O_3$ appears to be required to achieve adequate thermal stability.

It should be understood that, unless otherwise specified, when boron contents or ratios are expressed herein as $B_2O_3$, total boron content is intended, including boron present as aluminum borates and as free $B_2O_3$.

Conventional compounding procedures may be employed in compositing the two materials. It is necessary to provide an intimate admixture of the finely divided materials such as may be achieved by grinding, mulling, or ball milling the dry powders together, following which the mixture is shaped into a porous, self-supporting aggregate, as by tableting, prilling, extruding, casting or other well known techniques to form cylindrical pellets or extrudates, spheres or other granular forms ranging in size from about one/thirtytwo-inch up to about one-half-inch. For prilling, extruding, or casting, the powdered mixture is ordinarily wetted with sufficient water or other liquid to form a suitable plastic or flowable mixture, while tableting is ordinarily performed by compressing the slightly moist but sensibly dry powdered mixture into suitable tableting dies.

Instead of initially dry mixing the alumina and the boron compound, the powdered alumina can be homogenized into an aqueous or other solvent solution of boric acid to provide the proper consistency for prilling, spry drying, extruding, casting, coating or the like. Also, alumina powder can be impregnated with aqueous or other solvent solutions of boric acid and then calcined to form an alumina boria powder which can then be formed into any desired shape prior to the high temperature calcination to transform the alumina-boria to aluminum borate. A hydrous alumina gel, prepared by any of the many methods known in the art, can be peptized by the addition of boric acid in the desired amount, and the peptized gel can then be spray-dried by conventional methods to form an intimate alumina-boria mixture which can be subsequently transformed into a shaped aluminum borate. These methods, and other equivalent methods which give extremely intimate admixture, are preferred in that they permit the final calcination to be carried out at temperatures and/or times in the lower ranges described hereinafter. A particularly suitable class of solvents for these modifications comprises liquid aliphatic polyhydroxy compounds such as glycerol, glycols, and the like, in which boric acid is more soluble than in water.

In one form of casting or molding, a monolithic block may be prepared by incorporating suitable combustible fibrous material into the fluid slip, which is later removed by combustion to give a monolithic body traversed by suitable one-thirtysecond to one-fourth inch diameter chanels for fluid flow from one face of the monolith to the opposite face. Other conventional methods for fabricating monolithic structures may also be utilized.

Another form of monolithic support can be prepared by depositing a thin layer of the alumina-boric acid slurry (in water orother solvent) over the surfaces of a preformed monolith composed of inert, low-surface-area materials such as alpha alumina or cordierite, which in themselves possess insufficient surface area and/or porosity for catalytic purposes. Several such monolithic supports are commercially available, notably those composed of cordierite or spodumene in the form of corrugated septa consolidated together in layers or rolls to provide a multiplicity of parallel channels from about one-thirtytwo inch to one-fourth inch in diameter traversing the structure. To render these monoliths suitable for use herein it is desirable to coat the channel surfaces (external and internal) thereof with a layer of the alumina-boria composite ranging in thickness from about 0.0005 to 0.01 cm. This may be conveniently achieved by immersing the monolith in a water or glycerol solution of boric acid or other soluble boron compound in which the alumina component is dispersed to give a viscous slurry.

All of the above support forms comprise, after drying at temperatures of, e.g., 200°–600° F, a shaped, porous, cohesive aggregate of finely divided alumina and boria or boria precursor. The shaping into a porous, cohesive aggregate (whether granular, monolithic, or membraneous) preferably takes place prior to the critical calcination step. For purposes of this invention the term "aggregate" may be defined as a cohesive mass measuring at least about 0.0005 cm in at least one dimension. A "cohesive" aggregate is defined as one which retains its shape after boiling in water for 10 minutes. The porosity of the dried aggregate prior to calcining should be at least about 0.1 ml/g.

Minor proportions of other conventional refractory oxide support materials may also be admixed with the alumina-boria composite prior to the final shaping operation. Examples of such materials include silica, magnesia, zirconia, titania, and the like.

After drying, the shaped support is then subjected to the critical calcination step, as by heating in air or other gases for about 1–48, preferably 1–12 hours at temperatures between about 1250° and 2600° F, preferably about 1450°–23000° F. The operation may be carried out in conventional manner, as, e.g., in a rotary kiln, fired oven, by passing hot gases through a fixed bed of the support. It is preferable to raise the support material to the final caecining temperature over a period of about 1 to 5 hours. The overall severity of the calcination should be controlled to produce in the first instance a substantial, X-ray-detectable phase of crystalline $9Al_2O_3.2B_2O_3$, corresponding substantialy to the following diffraction pattern:

Table 1

| dA | I/I$_1$ | dA | I/I$_1$ | dA | I/I$_1$ |
|---|---|---|---|---|---|
| 7.49 | 10 | 2.42 | 60 | 1.856 | 40 |
| 5.33 | 100 | 2.30 | 60 | 1.836 | 80 |
| 5.25 | 60 | 2.27 | 40 | 1.814 | 80 |
| 4.35 | 100 | 2.25 | 80 | 1.782 | 40 |
| 3.81 | 60 | 2.17 | 100 | 1.771 | 60 |
| 3.72 | 80 | 2.16 | 60 | 1.717 | 40 |
| 3.40 | 60 | 2.106 | 80 | 1.706 | 60 |
| 3.35 | 100 | 2.09 | 40 | 1.685 | 40 |
| 3.10 | 40 | 2.00 | 20 | 1.679 | 80 |
| 2.82 | 80 | 1.94 | 60 | 1.585 | 80 |
| 2.67 | 100 | 1.935 | 20 | 1.560 | 80 |
| 2.64 | 60 | 1.916 | 40 | 1.550 | 60 |
| 2.495 | 100 | 1.87 | 60 | 1.525 | 40 |
|  |  |  |  | 1.507 | 100 |

This phase is normally produced in the form of well defined crystallites having an average size of about 75–250A, which are easily detectable by X-ray diffraction analysis. Preferred forms of the support will also comprise a relatively minor phase, believed to be $2Al_2O_3.B_2O_3$, in the form of smaller crystallities having an average size of about 1–30 A, and which are usually not as eadily detectable by X-ray analysis. This phase (which is believed to enhance mechanical and thermal stability) exhibits the following major spacings:

Table 2

| dA | I/I$_1$ | dA | I/I$_1$ | dA | I/I$_1$ | dA | I/I$_1$ |
|---|---|---|---|---|---|---|---|
| 15.4 | 60 | 3.33 | 80 | 2.054 | 60 | 1.638 | 80 |
| 7.44 | 40 | 3.29 | 60 | 2.038 | 40 | 1.552 | 100 |
| 6.56 | 60 | 2.93 | 60 | 1.981 | 40 | 1.531 | 60 |
| 5.29 | 100 | 2.76 | 80 | 1.949 | 60 | 1.488 | 100 |
| 5.23 | 100 | 2.65 | 100 | 1.912 | 60 | 1.470 | 80 |
| 4.90 | 100 | 2.60 | 100 | 1.812 | 80 | 1.424 | 80 |
| 4.27 | 80 | 2.44 | 100 | 1.783 | 60 |  |  |
| 3.74 | 40 | 2.38 | 40 | 1.776 | 80 |  |  |
| 3.65 | 40 | 2.21 | 80 | 1.736 | 20 |  |  |
| 3.58 | 60 | 2.134 | 100 | 1.712 | 40 |  |  |
| 3.55 | 80 | 2.122 | 60 | 1.679 | 20 |  |  |
| 3.36 | 80 | 2.085 | 80 | 1.664 | 60 |  |  |

The size of the crystallites produced in the calcination is the primary parameter governing critical functional aspects of the support, such as mechanical and thermal stability, porotisy, pore size distribution, and surface area. Calcination temperatures in the high ranges tend to produce larege crystallites with resultant reduction in surface area and increase in average pore size. Conversely, the lower temperature ranges tend to give smaller crystallites, higher surface areas and smaller pores. These parameters of pore size and surface area can thus be made to vary considerably, depending upon the intended use of the catalyst. In many catalytic processes extremely high surface areas and pore volumes are not required, or may even be detrimental. In any case, it is normally desirable to preserve at least about 1, preferably at least about 5, m²/gm of surface area, and at least about 0.1, preferably at least about 0.2, ml/g of total porosity.

When the ultimate catalyst is intended for use in the conversion of automobile exhuast gases, the calcining should be controlled so as to give a support having a surface area between about 5–150, preferably about 20–100 m²/gm, with a porosity of about 0.2–0.8, preferably 0.3–0.7 ml/gm.

One aspect of the invention, which is important in many processes in which the finished catalysts may be utilized, is to ensure that substantially no free boria is present in the support when the active metal component is added. Free $B_2O_3$ melts at about 860° F and develops a substantial vapor pressure at temperatures above about 1200° F. Hence, during calcination following the addition of active metal salts, and/or during subsequent use of the catalyst at high temperatures, any free boria becomes very mobile and active as liquid and/or vaor, and tends to combine with and deactivate most of the common transitional metal catalyst components. Also, if any water is present, volatile metaboric acid may be formed, which becomes very corrosive to ferrous metals at elevated temperatures, as is molten $B_2O_3$ itself. In contrast to the hydrothermal instability of $B_2O_3$, the compounds $9Al_2O_3.2B_2O_3$ and $2Al_2O_3.B_2O_3$ appear to be hydrothermally stable up to temperatures of at least about 3540° F and 1895° F, respectively.

The maximum boria content (25 weight-percent) specified herein correponds substantially to the compound $2Al_2O_3.B_2O_3$ (the "2:1" compound). The concentration of 13.3 weight-percent $B_2O_3$ corresponds to the compound $9Al_2O_3.2B_2O_3$ (the "9:2" compound). The intermediate concentrations correspond to mixtures of the 2:1 and 9:2 compounds. Boria contents below 13:3 percent correspond to mixtures of the 9:2 compound and free $Al_2O_3$. It would hence appear that in theory no free boria should be present in the final calcined supports. However, depending upon the intimacy of admixture of the initial alumina and boria components, the temperature and time of calcination and perhaps other factors, some free boria is usually present in the calcined composites. Also, at calcination temperatures above about 1035° C (1895° F), the 2:1 compound breaks down to form free boria and the 9:2 compound:

In all such cases where free boria is present in the calcined support, it is usually desirable to remove it, preferably prior to the addition of active metals. A number of effective methods have been developed, including primarily the following:

1. Calcination at temperatures above about 1800° F.
2. Steaming at temperatures above about 400° F.
3. Leaching with hot water at, e.g., 200°–400° F.
4. Leaching in 10–28% aqueous ammonia solutions at, e.g., 50°–120° F.
5. Any combination of the foregoing procedures.

The effectiveness of these treatments is illustrated by the following examples in which samples of an aluminum borate in the form of ⅛ inch extrudates calcined at 1800° F were subjected to the indicated treatments:

Table 3

| Sample | Treatment | Boron Content, Wt.% | Boron removal, % of total initially present |
|---|---|---|---|
| 1 | none | 6.91 | — |
| 2 | Steaming at 100° F for 16 hours | 6.75 | 2.3 |
| 3 | Calcination at 2200° F | 5.99 | 13.3 |

Table 3-continued

| Sample | Treatment | Boron Content, Wt.% | Boron removal, % of total initially present |
|---|---|---|---|
| | for 1 hour | | |
| 4 | Leaching with boiling water for 2 hours | 6.47 | 6.4 |
| 5 | Boiling water leaching for 2 hours + NH₄OH leaching for 1 hour | 5.92 | 14.3 |

Leaching with boiling water and/or with warm, concentrated NH₄OH solutions appear to be the most effective treatments. The effectiveness of calcination at 2200° F (Sample 3) is not readily apparent, for at that temperature some of the 2:1 compound was undoubtedly converted to the 9:2 compound and free boria. Upon gradual cooling however, this free boria would in theory combine with a portion of the 9:2 compound to reform the 2:1 compound.

To illustrate the utilitarian effect of removing free boria, two comparisons were made on exhaust gas conversion (oxidation), using in one experiment a catalyst (A) containing 24 weight-percent $B_2O_3$ in the support and from which free boria had not been removed, and in the other a catalyst (B) containing the same active metals, but supported on a base which had been leached in boiling water to reduce the $B_2O_3$ content to 18 weight-percent. The results were as follows:

Table 4

| Catalyst | Temperatures required for 50% Conversion, ° F | | | |
|---|---|---|---|---|
| | Hydrocarbons | | Carbon Monoxide | |
| | Run 1 | Run 2 | Run 1 | Run 2 |
| A | 837 | 804 | 934 | 811 |
| B | 581 | 604 | 523 | 513 |

It is thus apparent that removing free boria from catalyst B resulted in at least about a 200° temperature advantage for hydrocarbon conversion and a 300° advantage for CO conversion.

By virtue of the foregoing methods for removing free $B_2O_3$, it is feasible to employ initially a substantial excess of boria or boria precursor, over the proportion desired in the final support, whereby essentially all of the alumina can be reacted at shorter calcination times and/or lower temperatures. In many cases it is desirable to provide a support containing substantially no free $Al_2O_3$, in order to prevent the formation during subsequent use of relatively inactive aluminates or spinels of the active metal or metals supported thereon. By the techniques described above it is entirely feasible to prepare supports containing less than about 1 weight-percent of free $B_2O_3$ and less than about 5 weight-percent of free $Al_2O_3$. However, in utilizing this excess-boria technique, not more than about 40 weight-percent, preferably less than about 30 weight-percent of boria should be employed in the initial aluminia-boria mixture. If too large an excess of boria is utilized, such that more than about 10–20 weight-percent of free $B_2O_3$ remains in the calcined aggregates, such aggregates will tend to disintegrate into a powder or slurry upon subsequent removal of the excess free boria (see U.S. Pat. No. 3,080,242). An important attribute of the calcined supports prepared as herein prescribed is their mechanical strength, which normally exceeds that corresponding to a crushing strength of 20 pounds for ⅛ × ⅛ inch extrudate pellets.

Following calcination and removal of free boria, the support may be impregnated in conventional manner with a solution or solutions of the desired catalytic metal salt or salts. Any one or more of the transitional metals or compounds thereof may be utilized, the more widely used of such being the metals of Groups IB, IIB, VB, VIB, VIIB, and VIII of the Periodic Table, and their oxides and sulfides. Exemplary metals are zinc, cadmium, copper, silver, chromium, molybdenum, tungsten, manganese, rhenium, iron, cobalt, nickel, ruthenium, rhodium, palladium, osmium, iridium, and platinum. In exhaust gas conversion catalysts, the more commonly used metals are copper, chromium, molybdenum, manganese, iron, cobalt, nickel, ruthenium, palladium ad platinum, or combinations thereof. The iron group metals, and the metals of Groups IB, IIB, VB, VIB and VIIB are normally employed in proportions ranging between about 3 percent and 30 percent, preferably about 6–20 percent by weight, based on the corresponding oxides. The Group VIII noble metals such as palladium and platinum are normally employed in smaller proportions of about 0.05–2 percent by weight.

The salts employed for impregnation are preferably those which are thermally decomposable to give the corresponding metal oxides and/or sulfides. Preferred salts are the nitrates, acetates, chlorides, oxalates, sulfates and the like. Following impregnation, the finished catayst are produced by draining, drying and if desired, calcining at temperatures of, e.g., 500° to 1000° F. In the final catalyst the active metal or metals may appear in the free form, as oxides or sulfides, or any other active form.

A preferred class of exhaust gas conversion catalysts comprises about 5–10 percent by weight of copper as CuO and about 5–15 weight-percent of iron, cobalt and/or nickel, as $Fe_2O_3$, $Co_3O_4$ or NiO. These metals, especially copper and iron, are apt to bring about severe shrinkage of conventional transition alumina supports at exhaust gas conversion temperatures. But when employed on the supports of this invention, the shrinkage is substantially nil.

Another preferred class of exhaust gas conversion catalysts comprises about 0.05 –1.0 weight-percent of one or more Group VIII noble metals, particularly platinum and/or palladium, together if desired with 1 to 10% of one or more of the metals, V, Cr, Mn, Co, Ni, Cu, and Zn.

USE OF CATALYSTS

Catalysts based on the supports of this invention may be employed to catalyze any chemical conversion in which supported active metals or metal compounds may advantageously be utilized. However, due to the remarkable thermal and hydrothermal stability of the supports, catalysts based thereon are most advantageously utilized in chemical conversions carried out at elevated temperatures of e.g., 600°–3000° F, and even more advantageously in processes requiring temperatures in the range of about 900°–3000° F.

Several general rules can be followed in selecting an optimum support for the particular reaction concerned. Firstly, for reactions carried out at above about 1900° F, it is preferred to utilize a support containing less than about 15 weight-percent, preferably less than 13 weight-percent of $B_2O_3$, so as to eliminate or minimize the formation of liquid $B_2O_3$ resulting from the conversion of the 2:1 aluminum borate to the 9:2 compound. For reactions carried out at below about 1900° F, it is preferred to utilize supports containing about 13–25 weight-percent of $B_2O_3$, so as to obtain maximum mechanical stability and surface area. It is also a general though not infallible rule that reactions carried out at very high temperatures with all reactants in the vapor phase require less porosity and surface area in the support than do reactions carried out at relatively low temperatures and/or with one or more of the reactants in the liquid phase. Where liquid phase reactants are involved, it is hence preferred to utilize supports having a porosity of at least about 0.5 ml/g, and a surface area above about 40 m$^2$/g. For vapor phase reactions carried out at temperatures above about 1200° F, it is normally feasible to utilize supports having surface areas in the low range of about 1–20 m$^2$g, and porosities in the range of about 0.2–0.7 ml/g. For low temperature vapor phase reactions, somewhat higher surface areas and pore volumes are generally desirable.

Another factor to be considered in selecting a suitable support is the amount and type of active metal or metals to be added thereto, and the degree of its dispersion on the support. Obviously, where high metal loadings are desired, a primary consideration is high porosity. Generally, higher porosity is obtained at the higher calcining temperatures. In cases where the active metal or metals are added to the support in such manner as to obtain a very high degree of dispersion thereon a relatively low surface area support may suffice, whereas higher surface areas may be required if the active component is not highly dispersed. With the aid of a minimum of judicious experimentation, these general guidelines can be used to effectively arrive at optimum aluminum borate supports for the particular chemical reaction concerned.

Depending to some extent upon the particular reaction involved, any conventional catalytic contacting technique may be employed, including fixed bed, moving bed, fluidized bed and slurry contacting procedures. Normally, a fixed bed operation is preferred with the reactants being passed in vapor phase, liquid phase, or mixed phase through a bed of macropellets of catalyst.

While it is obviously impossible to cite all possible chemical reactions in which the catalysts of this invention may be utilized, some of the more important and representative examples are: exhaust gas reduction to convert nitrogen oxides, exhaust gas oxidation to oxidize unburned hydrocarbons and carbon monoxide, methanation (hydrogenation of carbon oxides), steam reforming of methane or other light hydrocarbons to produce hydrogen or low BTU fuel gas, dehydrocyclization of $C_6$$^+$ paraffins to produce corresponding aromatic hydrocarbons, dehydrogenation of paraffins to form olfins, or of cycloparaffins to form aromatic hydrocarbons, naphtha reforming to produce high octane gasoline, hydrodealkylation of alkyl aromatic compounds to effect scission of paraffinic side chains from aromatic rings, hydrogenation of olefins and/or aromatic hydrocarbons, hydrodesulfurization and/or hydrodenitrogenation of mineral oils or fractions thereof, etc.

As previously indicated, catalysts of this invention are particularly useful for the conversion of nitrogen oxides, unburned hydrocarbons and carbon monoxide in internal combustion engine exhaust gases. Exhaust gases in the exhaust manifold normally attain temperatures of 1200°–1600° F, and peak temperatures in downstream catalytic converters can exceed 2,000° F, particularly when the exhaust is rich in unburned hydrocarbons which, with the aid of added air, are being oxidized in the converter. At these temperatures most catalysts lose substantially all of their activity, usually as a result of the formation of inactive combinations between the active catalyst component and the support. However, catalysts based on the supports of this invention are found to maintain their activity for converting nitrogen oxides, hydrocarbons and carbon monoxide at temperatures in excess of 2000° F. A particularly suitable exhaust gas conversion catalyst comprises about 5–10 weight-percent of copper as CuO and about 5–5 weight-percent of nickel as NiO.

The hydrogenation of carbon oxides (methanation) to produce methane is generally carried out at temperatures ranging between about 600° and 1500° F and pressure between about 100 and 1500 psig. The reaction is extremely exothermic, and much difficulty has been encountered in controlling temperature rise in the reactor. One widely used technique involves the recycle of large volumes of product gases (mainly methane) merely to serve as a heat sink, thus adding greatly to operating costs. Catalysts previously available for this purpose have been found to become substantially deactivated if temperatures in excess of about 1100°–1200° are reached during methanation, to the extent that they will not initiate the reaction at temperatures below about 1200° F. Some activity at temperatures about 1200° F, is usually retained, but at these high temperatures the equilibrium for methanation is unfavorable; it is therefore a practical necessity to carry out a substantial portion of the methanation at temperatures below 1200° F. However, it is also desirable to have a catalyst which does not place a "ceiling" on the permissible exothermic temperature rise; by removing this ceiling the need for expensive temperature control measures is reduced or eliminated.

It will hence be apparent that in methanation a catalyst active over the entire temperature range of about 500°–1500° F, and especially at temperatures above 1200° F, is highly desirable. Also, since steam is produced during methanation, a hydrothermally stable catalyst is also required. The catalysts of this invention appear to be ideally suited to these requirements. Metals active as methanation catalysts include primarily the Group VIII metals, and particularly nickel, or nickel promoted with cerium. Preferred methanation catalysts for use herein comprise about 5–40 weight-percent of nickel as NiO supported on the aluminum borate bases of this invention.

Steam reforming of methane, or $C_2$–$C_6$ paraffins, to produce hydrogen is the endothermic reverse of the methanation reaction, and is normally carried out at temperatures ranging between about 1500° and 2000° F. The high temperatures and presence of steam again present a problem in activity maintenance, since the same type of catalysts used for methanation are ordinarily used for steam reforming. Here again the catalysts of this invention find particular utility by virtue of their hydrothermal stability and activity maintenance.

Dehydrocyclization reactions are normally carried out at temperatures of about 850°–1150° F and pressures of about 0–50 psig. Primary feedstocks comprise paraffin hydrocarbons, preferably normal paraffins, having at least six carbon atoms, e.g., n-hexane, n-heptane, n-octane and the like, the corresponding products comprising mainly benzene, toluene, xylene and the like. Active catalytic components for dehydrocyclization comprise between about 0.1–20 weight-percent of one or more hydrogenating metals, preferably the metals of Group VIB and/or VIII, e.g., nickel, palladium, platinum, molybdenum, etc., and the oxides and sulfides thereof.

Dehydrogenation reactions are carried out under the same general conditions described above for dehydrocyclization, and the same type of active catalytic components are utilized. Substantially any paraffinic or alkyl aromatic hydrocarbon may be dehydrogenated to corresponding unsaturated compounds. For example ethane may be converted to ethylene, propane to propylene, butane to butene or butadiene, cyclohexane to benzene, methyl cyclohexane to toluene, ethylbenzene to styrene, etc.

Naphtha reforming operations are preferably carried out at temperatures of about 800°–1000° F, hydrogen pressures ranging between about 100 and 600 psig, and liquid hourly space velocities of about 0.5–5. Preferred feedstocks comprise straight run and/or cracked naphthas boiling in the range of about 200°–450° F, while the preferred active catalytic components comprise Group VIII noble metals, particularly platinum, employed in amounts of about 0.1–2 weight-percent.

In catalytic hydrodealkylation, the objective is to effect scission of paraffinic side chains from aromatic rings without substantially hydrogenating the ring structure. To accomplish this objective, relatively high temperatures in the range of about 800°–1200° are employed at moderate hydrogen pressures of about 300–1000 psig. Operative catalytic components comprise about 0.1–20 weight-percent of one or more hydrogenating metals, preferably metals of Group VIB and/or Group VIII, e.g., nickel, palladium, platinum, molybdenum and the like, or their oxides or sulfides.

In catalytic hydrofining, the primary objective is to effect a selective hydrodecomposition of organic sulfur and/or nitrogen compounds in the feed, without substantially cracking hydrocarbon molecules. For this purpose, temperatures in the range of about 500°–800° F, and pressures in the range of about 400–2000 psig are normally utilized. Operative catalytic components comprise the metals of Group VIB and/or Group VIII, preferably in sulfided form. Preferrred components comprise combinations of nickel and/or cobalt with molybdenum and/or tungsten. Principal feedstocks include gasoline fractions, kerosenes, jet fuel fractions, diesel fractions, light and heavy gas oils, crude oil residua and the like.

The following examples are cited to illustrate the invention, but are not to be construed as limiting in scope:

EXAMPLE 1–6

Boehmite alumina powder was ball milled and dry mulled with sufficient powdered boric acid to provide a 20% $B_2O_3$ — 80% $Al_2O_3$ composite, and the homogeneous powder was then mixed with sufficient dilute nitric acid to provide an extrudable plastic mass. The mixture was then extruded into ⅛-inch diameter pellets and dried. Separate portions thereof were then calcined at various temperatures as indicated in Table 1, for 24 hours. The samples calcined at 1200° and 1400° F were amorphous, while those calcined at the higher temperatures were highly crystalline. Each of the calcined samples were then impregnated with an aqueous solution of copper nitrate and cobalt nitrate to provide about 4% copper as CuO and 12% cobalt as $Co_2O_3$ in the final catalyst. After draining and drying at 110° C, the catalyst were tested for nitric oxide conversion activity and selectivity, using as the feed a synthetic exhaust gas having the following composition:

|  | Mole - % |  |
|---|---|---|
| CO | 1.0 |  |
| $H_2$ | 0.33 |  |
| $C_3H_6$ | 0.10 |  |
| NO | 0.08 |  |
| $H_2O$ | 10.0 |  |
| Air ($O_2$) | 1.43 | (0.3) |
| $CO_2$ | 13.0 |  |
| $N_2$ | 74.06 |  |
|  | 100.00 |  |

The test procedure consisted in passing the feed gas through the catalyst bed at a gaseous hourly space velocity of 23,000, measuring NO conversion at about 1000° F (which generally gives 100% conversion), then at successively lower temperature so as to bracket the 50% conversion temperature and obtain temperature coefficients. From this the 50% conversion temperatures were calculated, based on the first-order rate equation. Selectivity of conversion to nitrogen was determined at 1250° F. ("Selectivity" is the percent of NO converted which was converted to $N_2$ rather than to $NH_3$. The latter is undesirable because in most catalytic exhaust gas converters, any ammonia formed is ultimately oxidized back to NO and emitted to the atmosphere as a pollutant.) The results of the test runs were as follows:

Table 5

|  |  | Conversion of NO |  |
|---|---|---|---|
| Catalyst | Precalcination Temp., ° F | Temp., ° F for 50% Conversion | Selectivity to $N_2$, % |
| 1 | 1,200 | 920 | 53 |
| 2 | 1,400 | 933 | 66 |
| 3 | 1,600 | 760 | 86 |
| 4 | 1,800 | 740 | 86 |
| 5 | 2,000 | 817 | 63 |
| 6 | 2,200 | 765 | 82 |

It is readily apparent that catalysts 3–6, based on supports which were calcined at temperatures within the preferred range of the invention, were substantially more active and in most cases more selective than catalyst 1 and 2, based on supports calcined at temperatures below the preferred range. It should not be concluded however that the temperature range of 1250°–1400° F is inherently inoperable; as will be shown hereinafter this temperature range is effective when preferred support preparation techniques are utilized.

EXAMPLES 7–10

Four additional catalyst were prepared as described in Examples 1–6, with the exception that the $Al_2O_3/B_2O_3$ weight-ratio was 86/14 instead of 80/20. Upon testing as described in Examples 1–6, the following results were obtained:

Table 6

|  | Support | Conversion of NO |  |
|---|---|---|---|
| Catalyst | Precalcination Temp., ° F | Temp., ° F for 50% Conversion | Selectivity to $N_2$, % |
| 7 | 1,200 (amorphous) | 840 | 56 |

Table 6-continued

|  | Support | Conversion of NO |  |
|---|---|---|---|
| Catalyst | Precalcination Temp., ° F | Temp., ° F for 50% Conversion | Selectivity to $N_2$, % |
| 8 | 1,400 (amorphous) | 860 | 48 |
| 9 | 1,600 (crystalline) | 675 | 94 |
| 10 | 1,800 (crystalline) | 672 | 94 |

Here again, the superiority of the crystalline supports of this invention is readily apparent.

EXAMPLES 11–16

Six additional catalyst were prepared as described in Examples 1–6, except that the catalyst loading was 8% copper as CuO and 8% cobalt as $Co_2O_3$, and in two cases gibbsite alumina was used instead of boehmite. Upon testing as described in Examples 1–6, the following results were obtained:

Table 7

|  | Support | Conversion of NO |  |
|---|---|---|---|
| Catalyst | Precalcination Temp., ° F | Temp., ° F for 50% Conversion | Selectivity to $N_2$, % |
| 11 (boehmite) | 1,200 (amorphous) | 945 | — |
| 12 (boehmite) | 1,400 (amorphous) | 895 | 59 |
| 13 (boehmite) | 1,600 (crystalline) | 700 | 84 |
| 14 (boehmite) | 1,800 (crystalline) | 690 | 82 |
| 15 (gibbsite) | 1,400 (amorphous) | 820 | 85 |
| 16 (gibbsite) | 1,600 (crystalline) | 690 | 90 |

Gibbsite alumina thus appears to be somewhat more effective than boehmite alumina in the catalyst supports of this invention.

EXAMPLE 17

This example, and the following Example 18, illustrate more specifically certain preferred methods for preparing the support of this invention, as well as the effect of calcination temperature on surface area and crystallinity.

About 150 ml of dilute nitric acid solution (pH — 2.5), 50 g of Mallinckrodt analytical reagent grade boric acid powder, and 80 g of Kaiser boehmite alumina powder were mixed together in a blender to form a milk. Stirring was continued for an additional 15 minutes, whereupon the temperature of the mixture increased to ~175° F, and its consistency was that of a fluffy paste. An additional 52 g of boehmite were added to the paste and the mixture was hand stirred with a spatula to form a homogeneous thick heavy paste. The paste was injected into rubber casting mats (forming molds), and the filled mats were then placed in a drying oven and dried in air at a temperature of 110° C for 3 hours. Following the drying step, the pellets were removed from the casting mats with an ejection punch. The cast pellets, comprising 20 weight-percent $B_2O_3$, were hard, strong, and exhibited good form. Individual samples of the pellets were then given various air calcination treatments with the following results:

Table 8

| Support Sample | Calcination Temp., °F | Time, Hrs. | Surface Area, m²/g | Crystallinity |
|---|---|---|---|---|
| A | 1200 | 2 | 257 | Amorphous |
| B | 1550 | 3 | 99 | Crystalline |
| C | 1800 | 3 | 41 | Crystalline |
| D | 2000 | 3 | 27 | Crystalline |

In support A, approximately 30 percent of the pore volume is in pores of greater than 100 A diameter, whereas in support B almost 100 percent of the pore volume is in pores of diameter greater than 100 A.

EXAMPLE 18

About 250 g of ground Mallinckrodt analytical reagent grade boric acid powder and 660 g of Kaiser boehmite alumina powder were mixed together and dry mulled for 30 minutes. Mulling was then continued with a steady slow addition of dilute nitric acid solution (pH = 2.0). The time of wet mulling was 45 minutes, and 564 ml of nitric acid solution was used. The finished mull was placed in a barrel-plunger type extruder and extruded through a ⅛ inch diameter die at a pressure of 800 psig. The extrudates were air-dried at room temperature for 16 hours, and then broken up into the desired lengths (one-fourth inch to one-half inch). Individual samples of the extrudates were then given various air calcination treatments, with the following results:

Table 9

| Support Sample | Calcination Temp., °F | Time, Hrs. | Surface Area, m²/g | Crystallinity |
|---|---|---|---|---|
| E | 1200 | 2 | 296 | Amorphous |
| F | 2000 | 3 | 38 | Crystalline |

EXAMPLE 19

A suitable monolithic catalyst support was prepared as follows:

To 250 ml of glycerol was added over a 15 minute period 100 g of Kaiser boehmite alumina while stirring and heating to 145° C, at which temperature the slurry was aged for 1 hour. An additional 28 g of boehmite was added, followed by aging an additional 20 minutes. Then 33.8 g of granular boric acid was added, whereupon the slurry became thinner and the temperature dropped to 125° C. After aging for 35 minutes, an additional 15 g of boric acid was added, followed by aging an additional 65 minutes. The slurry then appeared to be too viscous, so an additional 100 ml of glycerol was slowly added, followed by heating an additional 60 minutes.

Next, four American Lava uncoated cordierite monolithic supports, Al Si Mag 795, of the rolled corrugated type 12/8 were immersed in the slurry and soaked for 15 minutes at 135° C, after which they were removed and placed in Gooch crucibles where the excess coating was removed by vacuum stripping. In addition to suction below, an air jet was directed from above to clear the flow passages of the monolith of excess coating material. After stripping, the coated monoliths were air dried in an oven at 110° C for 30 minutes, then heated in a furnace to 1800° F over a 4-hour period and calcined at that temperature for 24 hours.

The surface area of the resulting monoliths were determined by nitrogen adsorption (BET) to be 30 m²/g. This monolith, when impregnated with about 8 weight-percent NiO and 8 weight-percent CuO, provides a highly active and selective $NO_x$ conversion catalyst, which is stable up to temperatures of at least about 2200° F.

EXAMPLE 20

This example demonstrates that crystalline supports can be prepared at calcination temperatures below 1400° F, if a preferred compounding procedure is employed:

About 650 g of boric acid powder were dissolved in 1700 ml of hot distilled water, and the solution temperature was raised to 97° C. 800 g of alumina powder (boehmite) were added to the boric acid solution with stirring over a period of 30 minutes. The slurried mixture was aged for 15 minutes, during which time its temperature increased from 94° to 103° C. The wet slurry was then transferred to a Büchner funnel where the excess solution was stripped away, and the filter cake was air-dried for 1 hour. The wet powder was then oven-dried at 220° F for 1 hour and calcined in air as follows: the temperature was increased from 100° to 800° F over a period of 12 hours, and then held constant at 800° F for 2 hours, followed by a slow (~ 16 hours) cooling to ambient temperature.

840 g of the calcined powder were placed in a muller and dry-ground for 30 minutes. 500 ml of concentrated $NH_3OH$ were added to the powder and mulling was continued for 10 minutes. Then 470 ml of distilled water were added and the mulling was continued for an additional 125 minutes. The mull was then extruded through a ⅛ inch diameter die at 600 psig using a piston-cylinder type extruder. The extrusions were dried at 110° C for 1½ hours in a forced air oven, broken up into small extrudates, and calcined as follows: the temperature was increased from 100°–1200° F over a period of 12 hours, held constant at 1200° F for 2 hours, and then cooled slowly (~16 hours) to ambient temperature. The properties of the calcined extrudates were as follows:

Table 10

Properties of Alumina-Boria Extrudates Calcined in Air at 1200° F

| | |
|---|---|
| Water Pore Volume | 0.65 cm³/g |
| Compacted Bulk Density | 0.51 g/cm³ |
| X-Ray Analysis | amorphous aumina-boria |

Various samples of the 1200° F calcined extrudates were calcined in air at 1300° F for period of from 1 to 16 hours, and then analyzed by X-ray diffraction to determine structure and composition. The results were as follows:

Table II

Effect of Calcination Time at 1300° F on the Crystalline Structure of Aluminum Borate Extrudates

| Calcination Time, hrs. | Crystalline Structure (Crystalline Size In Angstroms) |
|---|---|
| 1 | $9Al_2O_3 \cdot 2B_2O_3$ (trace) |
| 2 | $9Al_2O_3 \cdot 2B_2O_3$ (175) |
| 3 | $9Al_2O_3 \cdot 2B_2O_3$(125) + $2Al_2O_3 \cdot B_2O_3$ (trace) |
| 4 | $9Al_2O_3 \cdot 2B_2O_3$ (150) |
| 6 | $9Al_2O_3 \cdot 2B_2O_3$(125) + $2Al_2O_3 \cdot B_2O_3$ (trace) |
| 16 | $9Al_2O_3 \cdot 2B_2O_3$(150) + $2Al_2O_3 \cdot B_2O_3$ (trace) |

This method of preparation considerably reduces the severity of calcination treatment required for crystallization of the desired aluminum borate structure. This is attributed to the excellent dispersion of boric acid within a high surface area "activated" alumina afforded by this method of preparation. Any method which results in a high degree of dispersion of the boron compound in the alumina compound, i.e., good intimate contact between the reactants, will facilitate the solid state reaction between alumina and boria to form aluminum borate, and thus reduce the effective crystallization temperature. Another desirable method is to mix boric acid with a hydrous alumina gel and then spray dry the peptized hydrous gel.

EXAMPLE 21

This example illustrates the preparation of a preferred methanation catalyst of this invention.

An aluminum borate ⅛ inch extrudate support containing about 17 weight-percent $B_2O_3$ was prepared essentially as described in Example 20, but was calcined in air at 1800° F for 14 hours and then steamed at 1000° F for 24 hours. About 1520 g of $Ni(NO_3)_2 \cdot 6H_2O$ was dissolved in sufficient distilled water to give a total volume of 1000 ml. This solution was then used to impregnate 1000 ml of the support. After draining off excess solution, the impregnated extrudates were then calcined in air at temperatures gradually increasing from 100°–750° F over a 12 hour period, and held at 750° F for an additional 2 hours. Analysis of the resulting catalyst showed the following properties:

Table 12

| Catalyst Analysis | |
|---|---|
| Pore volume | 0.61 cm³/g |
| Compacted bulk density | 0.72 g/cm³ |
| BET surface area | 36 m²/g |
| Metal loading | 25.4 weight-percent NiO |
| X-ray analysis | $9Al_2O_3 \cdot 2B_2O_3$ (125 A) |
|  | NiO (250 A) |
|  | $2Al_2O_3 \cdot B_2O_3$ (trace) |

EXAMPLE 22

The catalyst of Example 21 was compared for methanation activity in a 6-day life test with a commercial methanation catalyst comprising about 25 weight-percent nickel supported on an activated $Al_2O_3$ base containing about 17 weight-percent of a calcium aluminate binder. The test unit consisted of a ¾ inch I.D. tube holding 50 ml of catalyst, giving a 7-inch bed depth, with a thermocouple well extending longitudinally through the catalyst bed so that exothermic temperature rises (ΔT's) at each inch of bed depth could be detected. With downflow of feed gas in this apparatus, the rate of progressive catalyst deactivation is measured by the rapidity with which the peak ΔT moves downwardly through the catalyst bed, signifying deactivation of the catalyst upstream from the peak ΔT.

Using a feed gas comprising 38.5% $CH_4$, 18.6% $H_2$, 5.0% $CO_2$ and 37.9% $H_2O$ by volume, and at a pressure of 300 psig and a dry gas space velocity of 5000 v/v/hr, the results were as follows:

Table 13

| Results with Catalyst of Example 21 | | | | | | |
|---|---|---|---|---|---|---|
| Days on Stream | 1 | 2 | 3 | 4 | 5 | 6 |
| Inlet Temp., ° F | 918 | 925 | 950 | 925 | 920 | 900 |
| Catalyst Bed Temp. ° F | | | | | | |
| Δ T First Inch | 117 | 163 | 175 | 180 | 160 | 180 |
| Δ T Second Inch | 38 | 47 | 35 | 50 | 60 | 70 |
| Δ T Third Inch | 0 | 0 | 0 | 0 | 0 | 0 |

Table 13-continued

| | | | | | | |
|---|---|---|---|---|---|---|
| Total Δ T | 155 | 215 | 210 | 230 | 220 | 250 |
| Results with Commercial Catalyst | | | | | | |
| Days on Stream | 1 | 2 | 3 | 4 | 5 | 6 |
| Inlet Temp., ° F | 893 | 915 | 905 | — | 920 | 918 |
| Catalyst Bed Temp. ° F | | | | | | |
| Δ T First Inch | 52 | 40 | 25 | — | 30 | 20 |
| Δ T Second Inch | 125 | 115 | 110 | — | 80 | 70 |
| Δ T Third Inch | 0 | 40 | 55 | — | 80 | 115 |
| Δ T Fourth Inch | 0 | 0 | 0 | — | 0 | 5 |
| Total Δ T | 177 | 195 | 190 | — | 190 | 210 |

The foregoing results show firstly that the Example 21 catalyst had a higher intrinsic activity than the commercial catalyst, for the inlet temperatures in the latter case were insufficient to initiate substantial reaction in the first inch of the catalyst bed, whereas in the former case the first inch of catalyst bed remained highly active throughout the 6-day run. Of even more importance however is the fact that the Example 21 catalyst showed no measureable deactivation, the reaction being driven to equilibrium in the first 2 inches of catalyst bed throughout the run. The commercial catalyst however was deactivating fairly rapidly, as evidenced by the decline in activity of the second inch of the bed and the rising activity appearing in the third and fourth inch. After about 20 days of operation in this manner, the entire bed of the commercial catalyst would be deactivated.

The following claims and their obvious equivalents are intended to define the true scope of the invention:

I claim:

1. A process for the hydrogenation of carbon oxides to produce methane, which comprises contacting a feed gas comprising hydrogen and an oxide of carbon with a catalyst comprising nickel dispersed on a porous, crystalline aluminum borate support at a temperature between about 600° and 1500° F, and recovering from said contacting a methane-enriched product gas, said aluminum borate support having a surface area of at least about 1 m²/g.

2. A process as defined in claim 1 wherein at least a portion of said hydrogenation is carried out at temperatures above about 1200° F.

3. A process as defined in claim 1 wherein said catalyst comprises about 5–40 weight-percent of nickel as NiO.

4. A process as defined in claim 1 wherein said aluminum borate support has a $B_2O_3/Al_2O_3$ weight ratio between about 8/92 and 25/75.

5. A process as defined in claim 4 wherein said catalyst comprises about 5–40 weight-percent of nickel as NiO.

6. A process for the hydrogenation of carbon oxides to produce methane, which comprises contacting a feed gas comprising hydrogen and carbon monoxide with a catalyst comprising nickel dispersed on a crystalline aluminum borate support at a temperature between about 600° and 1500° F, and recovering from said contacting a methane-enriched product gas, said catalyst having been prepared by the steps of:

1. intimately admixing finely divided alumina in a dry or hydrous state with sufficient boria or boria precursor to provide in the finished catalyst a $B_2O_3$/$Al_2O_3$ weight ratio between about 8/92 and 25/75;

3. forming the resulting mixture into aggregates of desired shape for catalytic contacting;

3. calcining the shaped aggregates for a time and at temperatures sufficient to form cohesive crystalline aluminum borate aggregates having a surface area between about 1 and 150 m²/g and a porosity of at least about 0.1 ml/g;
4. impregnating the calcined aggregates from step (3) with a nickel salt solution; and
5. calcining the impregnated aggregates to convert said nickel salt to a catalytically active form.

7. A process as defined in claim 6 wherein at least a portion of said hydrogenation is carried out at temperatures above about 1200° F.

8. A process as defined in claim 6 wherein said catalyst comprises about 5–40 weight-percent of nickel as NiO.

9. A process as defined in claim 6 wherein said calcining in step (3) is carried out at between about 1250° and 2600° F.

* * * * *